United States Patent
Tejani (10) Patent No.: US 9,987,117 B2
(45) Date of Patent: Jun. 5, 2018

(54) THROMBOEMBOLIC PROTECTION DEVICE

(71) Applicant: Furqan Tejani, Yonkers, NY (US)

(72) Inventor: Furqan Tejani, Yonkers, NY (US)

(73) Assignee: Furqan Tejani, Yonkers, NY (US)

( * ) Notice: Subject to any disclaimer, the term of this patent is extended or adjusted under 35 U.S.C. 154(b) by 167 days.

(21) Appl. No.: 14/534,538

(22) Filed: Nov. 6, 2014

(65) Prior Publication Data

US 2016/0128822 A1 May 12, 2016

(51) Int. Cl.
*A61F 2/01* (2006.01)

(52) U.S. Cl.
CPC .............. *A61F 2/013* (2013.01); *A61F 2/01* (2013.01); *A61F 2002/011* (2013.01); *A61F 2002/018* (2013.01); *A61F 2210/0014* (2013.01)

(58) Field of Classification Search
CPC ....... A61F 2002/018; A61F 2/01; A61F 2/013
USPC .................................................. 606/108, 200
See application file for complete search history.

(56) References Cited

U.S. PATENT DOCUMENTS

| | | | | |
|---|---|---|---|---|
| 6,030,414 A * | 2/2000 | Taheri | ....................... | A61F 2/07 623/1.1 |
| 6,139,517 A * | 10/2000 | Macoviak | ......... | A61M 25/1002 604/101.05 |
| 6,254,563 B1 * | 7/2001 | Macoviak | .......... | A61M 25/1011 604/101.05 |
| 6,361,545 B1 * | 3/2002 | Macoviak | ........ | A61B 17/12109 606/151 |
| 6,533,811 B1 * | 3/2003 | Ryan | ......................... | A61F 2/07 606/194 |
| 6,558,405 B1 * | 5/2003 | McInnes | ................. | A61F 2/013 606/200 |
| 6,709,415 B2 * | 3/2004 | Navia | .............. | A61B 17/12022 604/104 |
| 7,988,724 B2 * | 8/2011 | Salahieh | ............ | A61B 17/0644 623/2.12 |
| 8,114,114 B2 * | 2/2012 | Belson | ...................... | A61F 2/01 606/200 |
| 9,788,933 B2 * | 10/2017 | Sun | ........................... | A61F 2/07 |
| 2002/0004667 A1 * | 1/2002 | Adams | .................... | A61F 2/013 606/200 |
| 2002/0095171 A1 * | 7/2002 | Belef | ...................... | A61F 2/013 606/200 |
| 2002/0138094 A1 * | 9/2002 | Borillo | .................... | A61F 2/013 606/200 |

(Continued)

*Primary Examiner* — Dianne Dornbusch
(74) *Attorney, Agent, or Firm* — Schwabe, Williamson & Wyatt, P.C.

(57) ABSTRACT

Disclosed herein are systems and methods for protecting a subject from embolisms during TAVR percutaneous valve procedures. Various embodiments include an intravascular embolism protection device that includes an elongated, compliant wire frame made from a material having a shape-memory function, and a mesh sleeve coupled to the compliant wire frame, the mesh material having a pore size selected to allow blood to pass therethrough while retaining potential emboli. In some embodiments, the embolism protection device has a collapsed state wherein device fits within the lumen of a deployment/retrieval catheter and an expanded state wherein the embolism protection device expands to span the width of the aorta and the distance between the aortic valve and the puncture site in the femoral artery.

14 Claims, 9 Drawing Sheets

(56) References Cited

U.S. PATENT DOCUMENTS

| | | | | |
|---|---|---|---|---|
| 2002/0165576 | A1* | 11/2002 | Boyle | A61B 17/221 606/200 |
| 2003/0100940 | A1* | 5/2003 | Yodfat | A61F 2/01 623/1.15 |
| 2004/0243175 | A1* | 12/2004 | Don Michael | A61F 2/013 606/200 |
| 2006/0161241 | A1* | 7/2006 | Barbut | A61F 2/013 623/1.15 |
| 2006/0253148 | A1* | 11/2006 | Leone | A61B 17/12022 606/200 |
| 2007/0005103 | A1* | 1/2007 | Schaeffer | A61F 2/01 606/200 |
| 2007/0027534 | A1* | 2/2007 | Bergheim | A61F 2/013 623/2.11 |
| 2007/0208410 | A1* | 9/2007 | Berra | A61F 2/07 623/1.13 |
| 2008/0140110 | A1* | 6/2008 | Spence | A61F 2/06 606/200 |
| 2009/0254172 | A1* | 10/2009 | Grewe | A61F 2/856 623/1.15 |
| 2010/0168785 | A1* | 7/2010 | Parker | A61B 17/221 606/200 |
| 2010/0312268 | A1* | 12/2010 | Belson | A61F 2/01 606/200 |
| 2013/0096606 | A1* | 4/2013 | Bruchman | A61F 2/013 606/200 |
| 2013/0131714 | A1* | 5/2013 | Wang | A61F 2/01 606/200 |
| 2014/0052170 | A1* | 2/2014 | Heuser | A61F 2/013 606/200 |

* cited by examiner

THROMBOEMBOLIC PROTECTION DEVICE

TECHNICAL FIELD

Embodiments relate to a thromboembolic protection device that prevents the free flow of embolism-creating particles that are created during cardiac procedures such as percutaneous valve interventions, particularly transcatheter aortic valve replacement (TAVR) procedures, as well as coronary bypass surgery and other heart valve surgery.

BACKGROUND

An embolus can be any particle comprising a foreign or native material that enters the vascular system with potential to cause occlusion of blood flow. Emboli can be formed from aggregated fibrin, red blood cells, collagen, cholesterol, plaque, fat, calcified plaque, bubbles, arterial tissue, and/or other miscellaneous fragments. Each dislodged fragment, or embolus, is carried along by the blood flow until it becomes lodged or trapped in a smaller vessel and occludes blood flow, creating an embolism. Since emboli reduce or cut off blood flow, damage to the body may result, such as tissue damage, heart attack, stroke, or even death.

Percutaneous valve interventions include valvuloplasty, annuloplasty, and valve replacement surgeries performed on the mitral, tricuspid, aortic, and pulmonary valves. These interventions carry a high risk of embolism formation. For instance, aortic valve applications, such as transcatheter aortic valve replacement (TAVR) procedures, may carry a 60-80% chance of embolism formation and subsequent cerebral ischemic events.

BRIEF DESCRIPTION OF THE DRAWINGS

Embodiments will be readily understood by the following detailed description in conjunction with the accompanying drawings. Embodiments are illustrated by way of example and not by way of limitation in the figures of the accompanying drawings.

DETAILED DESCRIPTION OF DISCLOSED EMBODIMENTS

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "NB" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous.

Embodiments herein provide embolism protection devices that may be deployed in the arterial system for the collection of loosened or floating debris, such as embolic material dislodged during or thrombi formed as a result of percutaneous cardiac procedure, such as a valve intervention. In some embodiments, the device may be advanced through the vasculature using a right femoral artery approach, and it may be positioned so that it extends from and spans the distance between an opening in the right femoral artery, through the right iliac artery, and into the descending aorta, aortic arch, and ascending aorta in such a way that it covers all of the ostia of the major branches of the right iliac artery, descending aorta, aortic arch, and ascending aorta, such as the left and right renal arteries, the left subclavian artery, the left carotid artery, and the right carotid artery and right subclavian artery at the brachiocepahilc trunk. When so positioned, the embolism protection device excludes from the arterial system any plaques or other emboli that get dislodged, for example due to mechanical and drag forces exerted upon them as the various devices traverse the area of plaque. Thus, the device may prevent atherosclerotic material and other debris from entering the cerebral circulation, and may protect the subject from brain embolism associated with, for instance, percutaneous treatment or replacement of the aortic valve, or any coronary stent or bypass procedure. In some embodiments, the device may be particularly useful for TAVR procedures.

In other embodiments, the device may be used to protect the vasculature of a patient from dislodged materials (e.g., potential emboli and thrombi) from valvular or coronary artery disease, or during angioplasty, atherectomy, thrombectomy, embolectomy, intravascular diagnostic procedures, stent placement procedures, and/or any minimally invasive heart intervention. Embodiments of the device also may be used to protect a subject from emboli and thrombi resulting from open interventional procedures, including transapical approaches to treat valvular disease and cardiovascular bypass, as well as standard open coronary bypass and heart valve surgeries.

In various embodiments, the embolism protection device may take the form of an elongated, compliant tube having two layers: a thin, porous, mesh sleeve and a compliant wire support frame supporting the porous mesh sleeve from within the lumen of the mesh sleeve. In various embodiments, the porous mesh sleeve may be formed from a thin, hydrophilic mesh material having a pore size that is sufficiently large to allow blood to flow freely therethrough, but that is sufficiently small to prevent potential thrombi and emboli from passing through. In various embodiments, the hydrophilic mesh material may ease the insertion of the device into the vascular system, as it is slippery. In some embodiments, the hydrophilic mesh material may be made of material that is porous enough to permit the passage of blood therethrough, but that has pores that are too small for the atheromatous debris to get through.

In various embodiments, the compliant, elongated, tubular wire support frame may be formed from a material having a shape memory function, such as Nitinol™ wire. In various embodiments, the compliant wire support frame may fit within the porous mesh sleeve, and may be coupled to or otherwise configured to stabilize and/or stretch the porous mesh sleeve. In some embodiments, the wire frame may be biased to adopt an open configuration (e.g., having a larger diameter and a correspondingly larger lumen in the open state than in the closed state), and may be sized and shaped to secure or stretch the mesh sleeve in an open position when the wire frame is permitted to assume its natural shape, thus forming an elongated tube with a hollow lumen.

In various embodiments, the mesh sleeve and compliant wire support frame also may be compressed or collapsed to adopt a very small outer circumference and/or outer diameter, for instance by being inserted into the lumen of a small diameter deployment/retrieval catheter. In some embodiments, the deployment/retrieval catheter may be sized to fit within the lumen of a conventional TAVR sheath, such that the deployment/retrieval catheter containing the collapsed embolism protection device may be advanced therethrough to a desired part of the arterial system. In some embodiments, one or both ends of the deployment/retrieval catheter may be slightly flared, for instance to ease insertion of the embolism protection device into and/or deployment of the embolism protection device from the deployment/retrieval catheter.

In various embodiments, the embolism protection device may be configured to be advanced through the TAVR sheath in the femoral artery in a compressed state, for example along a guidewire and within the deployment/retrieval catheter, to a desired position within an artery, such as adjacent the aortic valve in the ascending aorta, where it may be released from the deployment/retrieval catheter and positioned in such a way as to protect all of the major arterial branches of the aorta simultaneously. For instance, once deployed, the embolism protection device may span the distance from the opening in the femoral artery into the right iliac artery, and from there, into the descending aorta, aortic arch, and ascending aorta. When released from the deployment/retrieval catheter (e.g., when the deployment catheter is retracted from the TAVR sheath, leaving the embolism protection device in place), the embolism protection device may expand to fit closely (yet atraumatically) against the artery walls, and may cover all of the ostia of the major branches of the right iliac artery, descending aorta, aortic arch, and ascending aorta, such as the left and right renal arteries, the left subclavian artery, the left carotid artery, and the right carotid artery and right subclavian artery at the brachio-cepahilc trunk.

In various embodiments, the mesh material of the porous mesh sleeve may have a pore size that is sized to allow vessel perfusion (e.g., that allows the passage of red blood cells), while still preventing potential emboli (e.g., atherothrombotic debris) from passing into an arterial branch. For example, in some embodiments, the mesh material may have a pore size of about 80-100 microns. In some embodiments, when the embolism protection device is deployed, the porous mesh sleeve may be stretched by the compliant wire support frame to form an elongated, porous mesh tube, the outer wall of which may fit closely against the full circumference of the inner wall of the artery, and may thereby extend across the ostia of a plurality of arterial branches, such as two, three, four, five, or even more arterial branches. Thus positioned, the embolism protection device any potential emboli that may otherwise pass into an arterial branch.

In various embodiments, the embolism protection device may have an elongated shape, with a length of about 300-500 mm or even longer, such as 550 mm, 600 mm, 650 mm, 700 mm, 750 mm, or even longer, and an expanded width of about 10-40 mm, such as 10 mm, 15 mm, 20 mm, 25 mm, 30 mm, or 35 mm, to ensure that the device is of sufficient size to span the width of the aorta at its widest point, and to cover all of the major arterial branches coming off of the aorta, if desired. For example, in some embodiments, the embolism protection device may be positioned with a distal end adjacent to the aortic valve, and a second end extending proximally out of the puncture site in the femoral artery. When positioned in this manner, the device may protect the entire circulation from emboli arising near the aortic valve, including both the anterior circulation (e.g., the carotid arteries) and the posterior circulation (e.g., the vertebral arteries). One of skill in the art will appreciate that the dimensions of the embolism protection device may be tailored to suit a particular procedure or subject. For instance, an infant, child, or small adult may require a shorter and/or narrower device, whereas a larger adult may require a longer and/or wider device in order to properly span the selected arterial branches and extend the full width of the aorta.

In use, in various embodiments, the embolism protection device may be advanced over a guidewire such as a TAD™ guidewire (Covidien, Mansfield Mass.), or another wire having a diameter of about 0.01-0.04 inches, such as about 0.014-0.035 inches. In various examples, the embolism protection device, in its collapsed state within the deployment/retrieval catheter, may be guided along the guidewire by simply feeding the deployment/retrieval catheter (with the collapsed device contained inside) into the puncture site in the femoral artery. In other embodiments, the deployment/retrieval catheter may be advanced to a desired position adjacent the aortic valve, and the embolism protection device may then be collapsed and advanced into the deployment/retrieval catheter to the desired location adjacent the aortic valve. In still other embodiments, the embolism protection device may be advanced to a desired location (either by advancing the embolism protection device and deployment/retrieval catheter together, or by feeding the embolism protection device into an already-placed deployment/retrieval catheter) by coupling a wire to a proximal end or other portion of the embolism protection device via a hook or other coupling member, and then advancing the wire, thereby advancing the embolism protection device.

In various embodiments, once the embolism protection device has been delivered to the desired location, the deployment/retrieval catheter may be withdrawn, allowing the device to self-expand, thus protecting a plurality of arterial branches. Once the cardiac or vascular procedure has been completed, the deployment/retrieval catheter may be advanced over the embolism protection device, collapsing it inside the lumen of the catheter, and permitting the device to be withdrawn from the body.

Figure 1A:
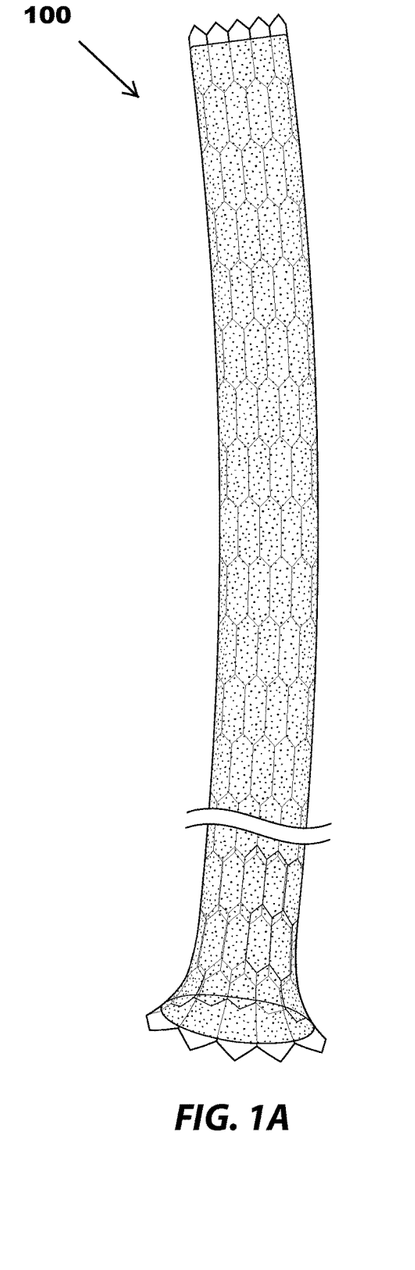
FIGS. 1A and 1B illustrate an example of an embolism protection device in an expanded state, shown in a perspective view (FIG. 1A) and a partial cutaway view (FIG. 1B)
Figure 1B:
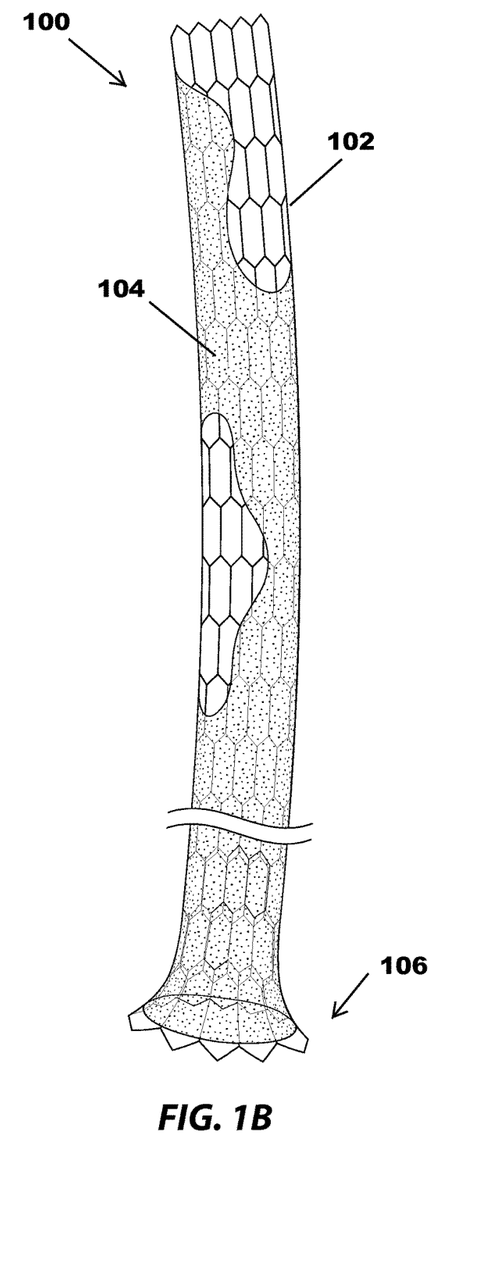

FIGS. 1A and 1B illustrate an example of an embolism protection device in an expanded state, shown in a perspective view (FIG. 1A) and a partial cutaway view (FIG. 1B), in accordance with various embodiments. As shown in FIG. 1A, the embolism protection device 100 may take the form of an elongated, compliant tube that is sized and shaped such that it may be inserted into an artery in a compressed state, and it may be biased such that it naturally assumes a tube shape having a hollow lumen when released. FIG. 1A shows the embolism protection device 100 in an open (e.g., non-compressed) state. As shown in FIG. 1B, the embolism protection device 100 may include two layers: a thin, porous, mesh sleeve 104 and a compliant wire support frame 102 supporting the porous mesh sleeve 104. In various embodiments, the porous mesh sleeve 104 may be formed from a thin, hydrophilic mesh material having a pore size that is sufficiently large to allow red blood cells and other blood components to flow freely therethrough, but that is sufficiently small to prevent potential thrombi and emboli from passing through. For example, in some embodiments, mesh material 104 may have a pore size of from about 80 microns to about 100 microns, or from about 90 microns to about 100 microns.

In various embodiments, the compliant wire support frame 102 may be formed from a material having a shape memory function, such as Nitinol™ wire. In some embodiments, the compliant wire support frame 102 may include a flared proximal end 106, which may help anchor the proximal end of the device as it protrudes from the body, for instance from the puncture site at the femoral artery. In various embodiments, mesh sleeve 104 may have a pore size that is sized to allow red blood cells and other blood components to pass freely therethrough, while still preventing potential emboli from passing into an arterial branch. For example, in some embodiments, mesh material 104 may have a pore size of from about 80 microns to about 100 microns, or from about 90 microns to about 100 microns.

Figure 2:
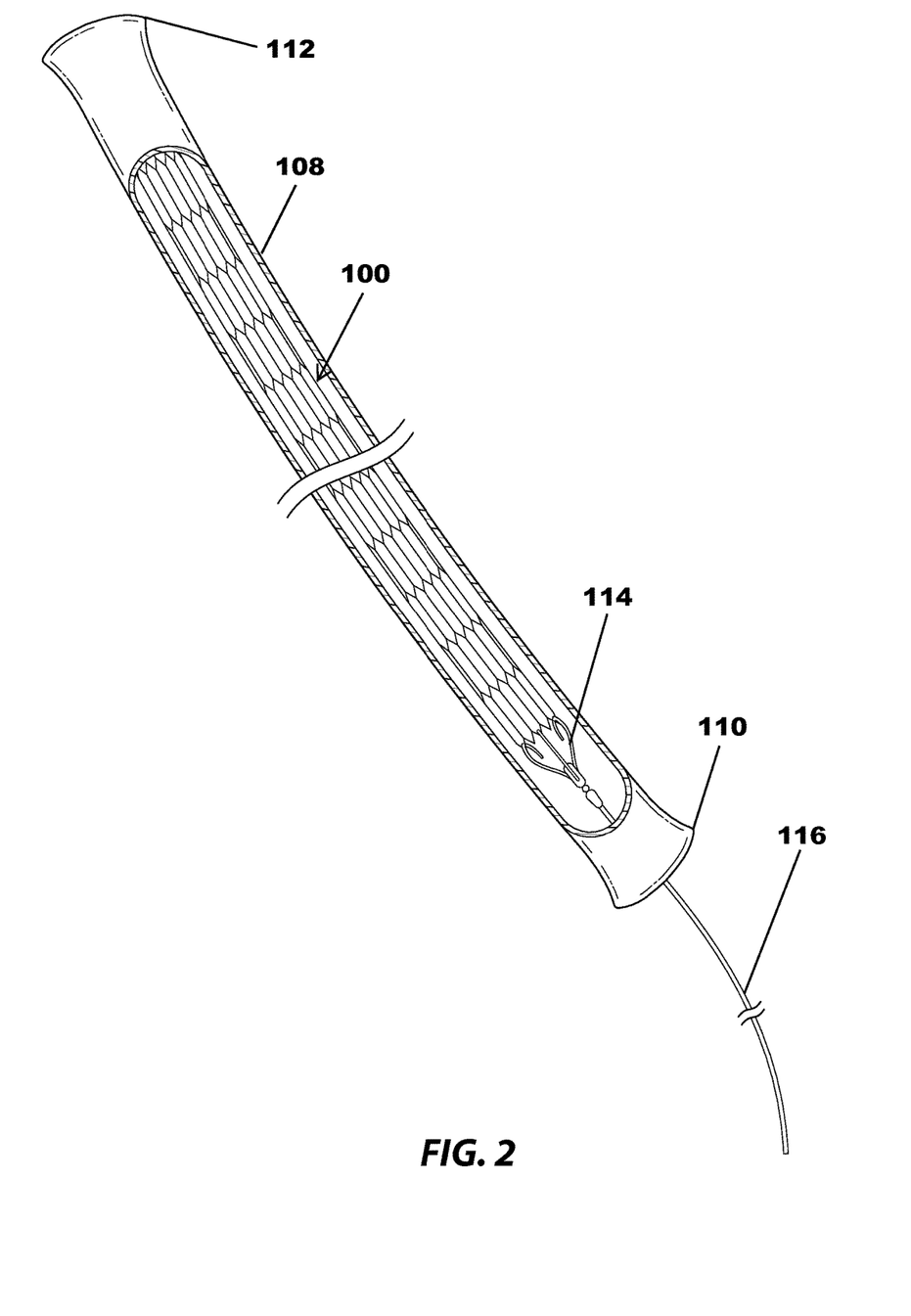
FIG. 2 illustrates the embolism protection device shown in FIGS. 1A and 1B in a compressed state inside a deployment/retrieval catheter.

FIG. 2 illustrates the embolism protection device shown in FIGS. 1A and 1B in a compressed state inside a deployment/retrieval catheter, in accordance with various embodiments. In some embodiments, the embolism protection device 100 may be collapsed when it is inserted into a narrow-diameter catheter, such as the illustrated deployment/retrieval catheter 108. In some embodiments, the proximal end 110 may include an outward flare, for example to aid in inserting the embolism protection device 100 into the deployment/retrieval catheter 108, and/or the distal end 112 may be flared, for example to aid in collapsing the embolism protection device 100 during retrieval. Although a single deployment/retrieval catheter is illustrated, one of skill in the art will appreciate that in some embodiments, separate catheters may be used for deployment and retrieval of the embolism protection device 100. In these embodiments, the deployment catheter (not shown) may have a flared proximal end and a non-flared distal end, whereas the retrieval catheter (not shown) may have a flared distal end and a non-flared proximal end. In some embodiments, neither end may be flared.

In some embodiments, the compressed embolism protection device 100 may be secured with a grasping member such as a hook member 114 coupled to a wire 116. In various embodiments, the hook member 114 and wire 116 may allow a user to advance or retract the embolism protection device 100 within the deployment/retrieval catheter 108.

Figure 3:
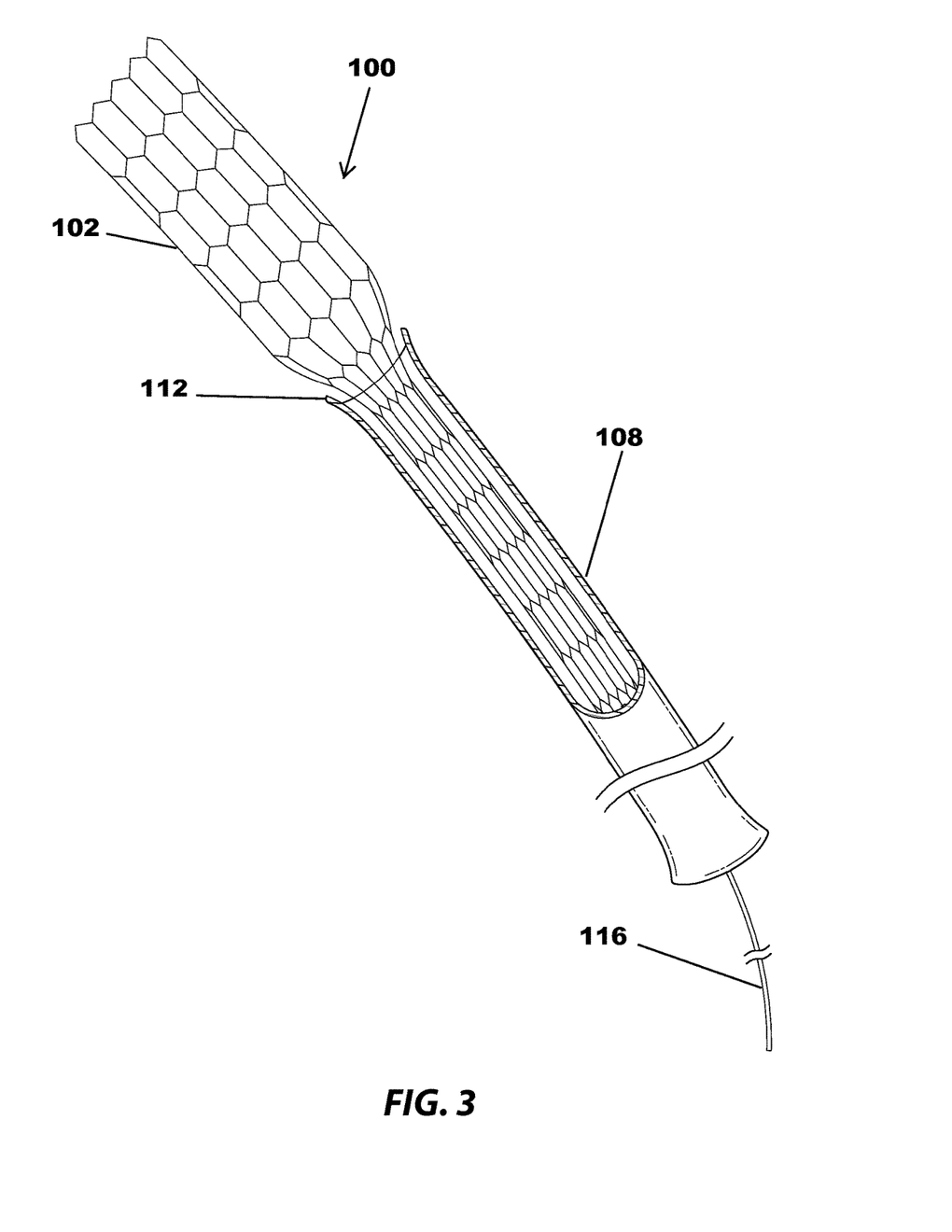
FIG. 3 illustrates the embolism protection device shown in FIGS. 1A and 1B in the process of being deployed from the deployment/retrieval catheter.

FIG. 3 illustrates the embolism protection device shown in FIGS. 1A and 1B in the process of being deployed from the deployment/retrieval catheter, in accordance with various embodiments. One the deployment/retrieval catheter 108 has been advanced to a desired position within the arterial system, such as adjacent the aortic valve, the embolism protection device 100 may be allowed to expand. In various embodiments, because the compliant wire support frame 102 is biased in an open position, withdrawing the deployment/retrieval catheter 108 while leaving the embolism protection device 100 in place may allow the compliant wire support frame to expand as it is released from the deployment/retrieval catheter 108. In some embodiments, wire 116 may be used to help hold the embolism protection device 100 in place while the deployment/retrieval catheter 108 is withdrawn. Although the mesh sleeve is not shown in FIG. 3, it fits closely around the wire support frame 102 as shown in FIG. 1.

Figure 4:
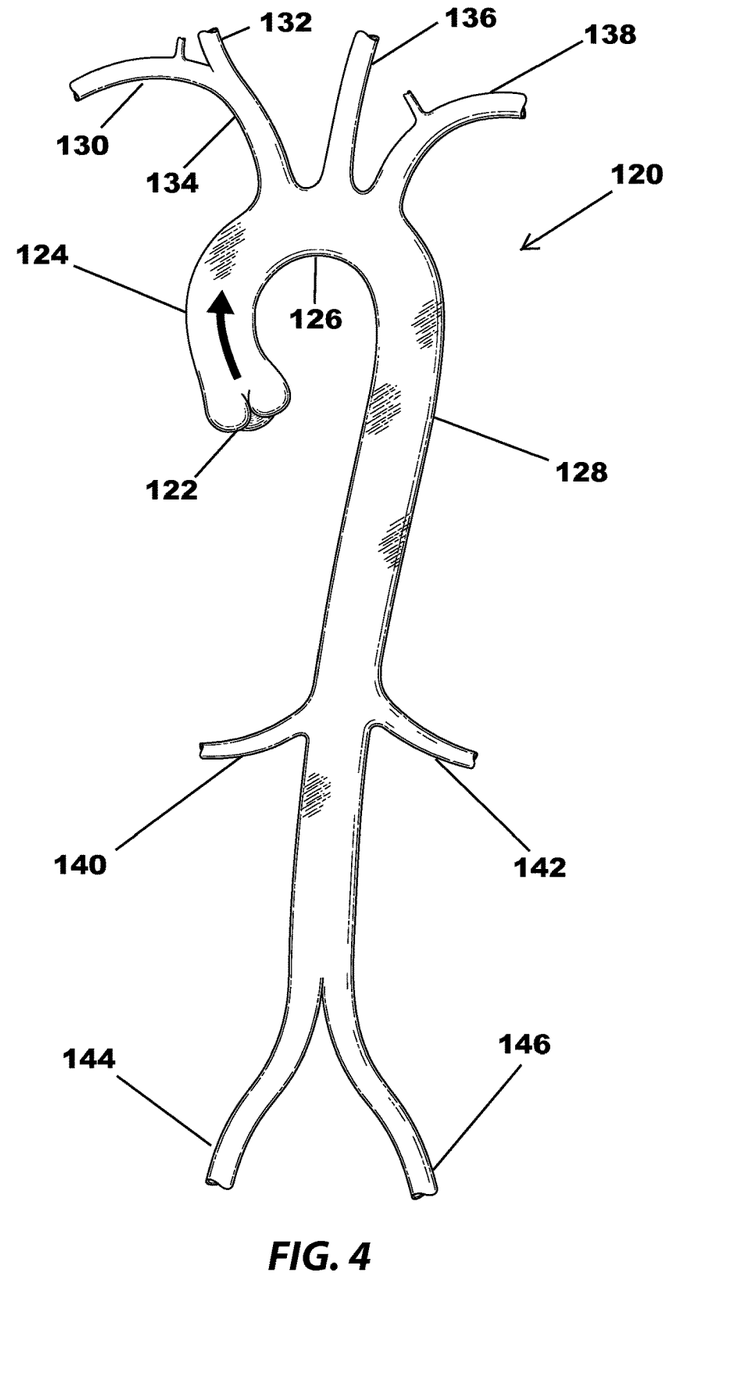
FIG. 4 illustrates the aorta and the major arterial branches extending therefrom.

FIG. 4 illustrates the aorta and the major arterial branches extending therefrom. The aorta 120 and aortic valve 122 are depicted, along with the ascending aorta 124, aortic arch 126, and descending aorta 128. Also shown are the major branches, including the right subclavian artery 130 and right carotid artery 132 at the brachio-cepahilc trunk 134, the left carotid artery 136, the left subclavian artery 138, the left 140 and right 142 renal arteries, and the left 144 and right 146 iliac arteries. In some embodiments, all of the ostia of the major branches of the aorta may be protected using the embolism protection devices disclosed herein.

Figure 5:
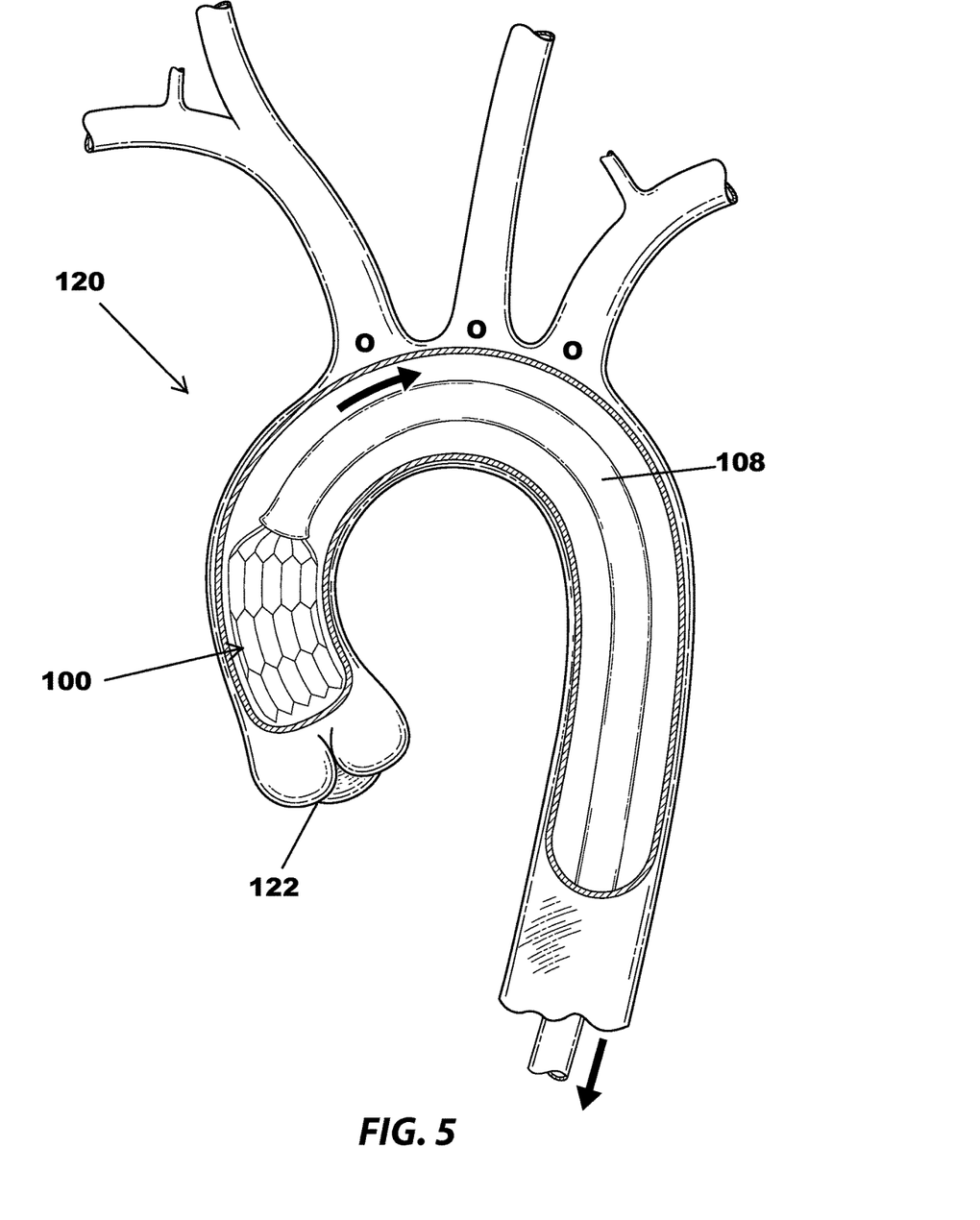
FIG. 5 illustrates the embolism protection device of FIGS. 1A and 1B being placed within the aorta prior to a TAVR procedure.

FIG. 5 illustrates the embolism protection device of FIGS. 1A and 1B being placed within the aorta prior to a TAVR procedure. In the illustrated embodiment, the embolism protection device 100 has been advanced through the aorta 120 in a collapsed state within the deployment/retrieval catheter 108 until it is adjacent the aortic valve 122. Once positioned, the deployment/retrieval catheter 108 may be withdrawn in a proximal direction, allowing the embolism protection device 100 to expand towards the artery walls, forming a mesh barrier along the ostia of the arterial branches O. So positioned and deployed, the embolism protection device 100 may prevent emboli from traveling from the TAVR procedure site to other parts of the arterial system.

Figure 6:
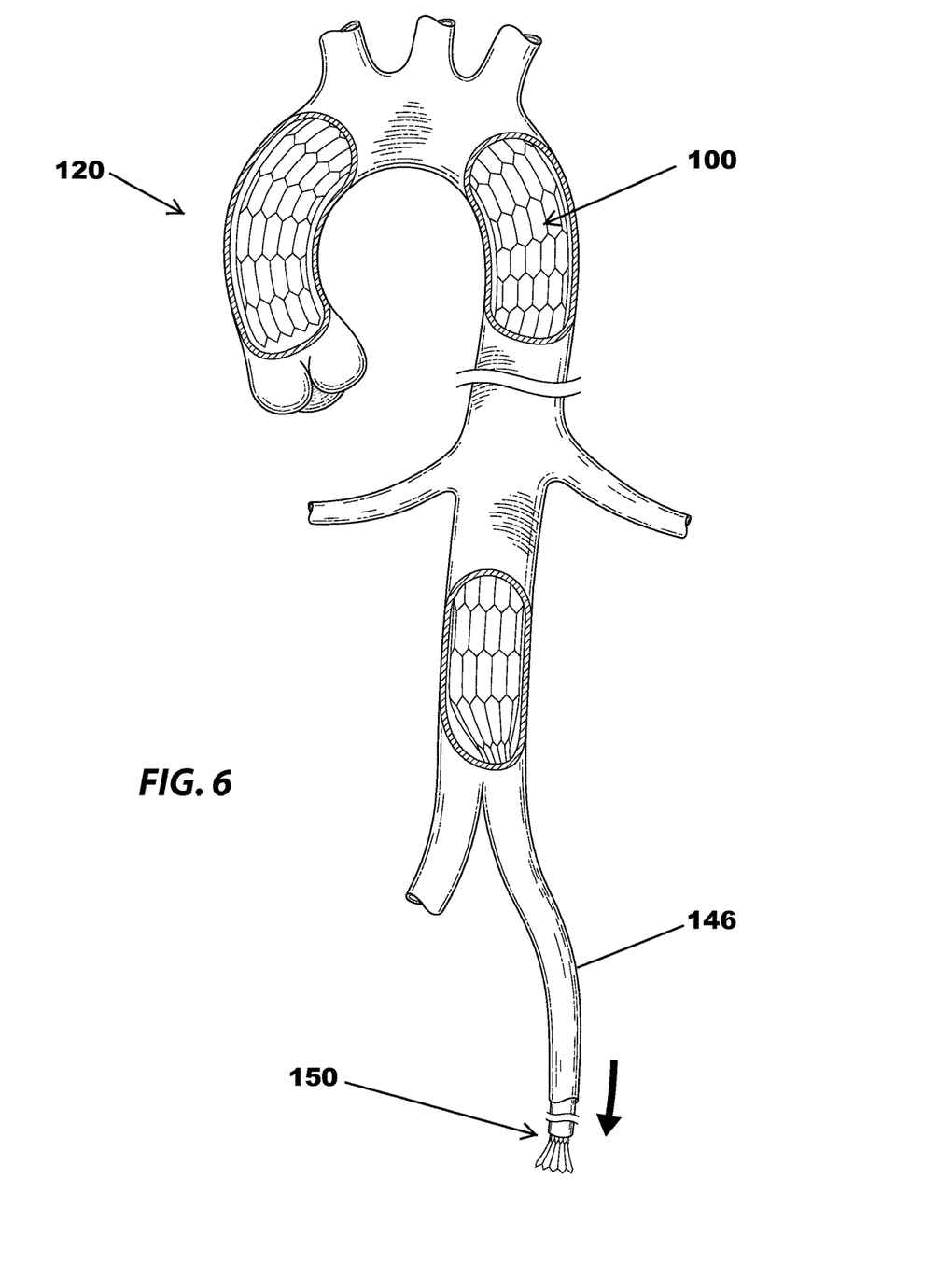
FIG. 6 illustrates the embolism protection device of FIGS. 1A and 1B lodged within the aorta and extending through the arterial system and out of a puncture in the femoral artery.

FIG. 6 illustrates the embolism protection device of FIGS. 1A and 1B lodged within the aorta and extending through the arterial system and out of a puncture in the femoral artery, in accordance with various embodiments. In the illustrated embodiment, the expanded embolism protection device 100 extends throughout the aorta 120, through the right iliac artery 146, and out of a puncture 150 in the right femoral artery.

Figure 7A:
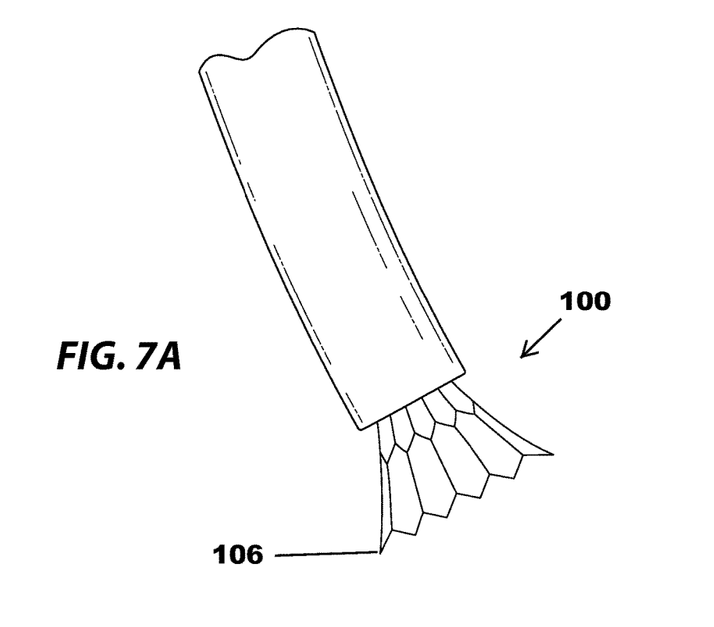
FIGS. 7A-7F illustrate an exemplary series of steps involved in removing the embolism protection device of FIGS. 1A and 1B from the body after a TAVR procedure has been performed, including identifying the flared end of the embolism protection device (FIG. 7A), manually pinching the flared end of the embolism protection device (FIG. 7B) to crimp the end (FIG. 7C), securing the crimped end of the embolism protection device with a snare (FIG. 7D), advancing the deployment/retrieval catheter over the embolism protection device (FIG. 7E), and removing the collapsed embolism protection device and deployment/retrieval catheter from the body of the subject (FIG. 7F); all in accordance with various embodiments.
Figure 7B:
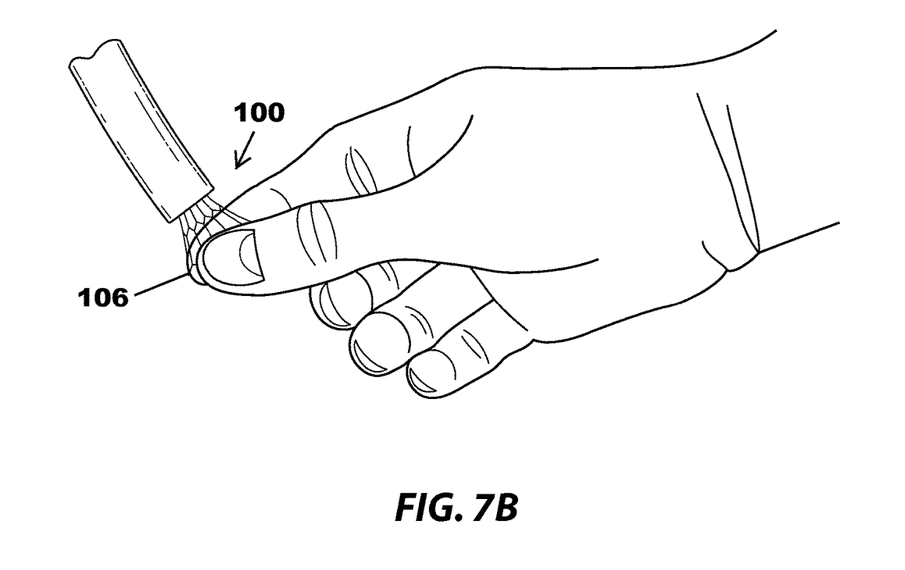
Figures 7C, 7D:
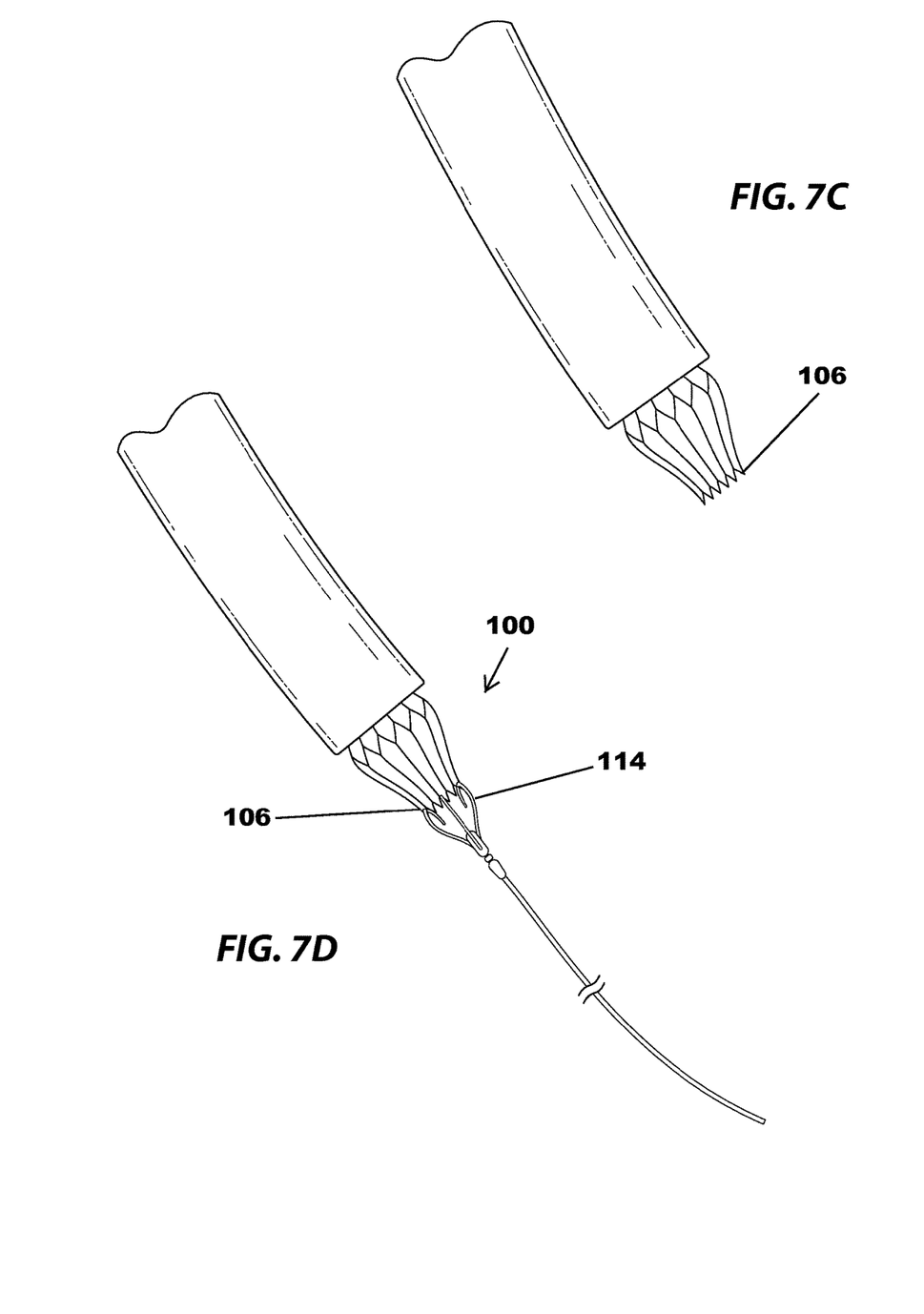
Figures 7E, 7F:
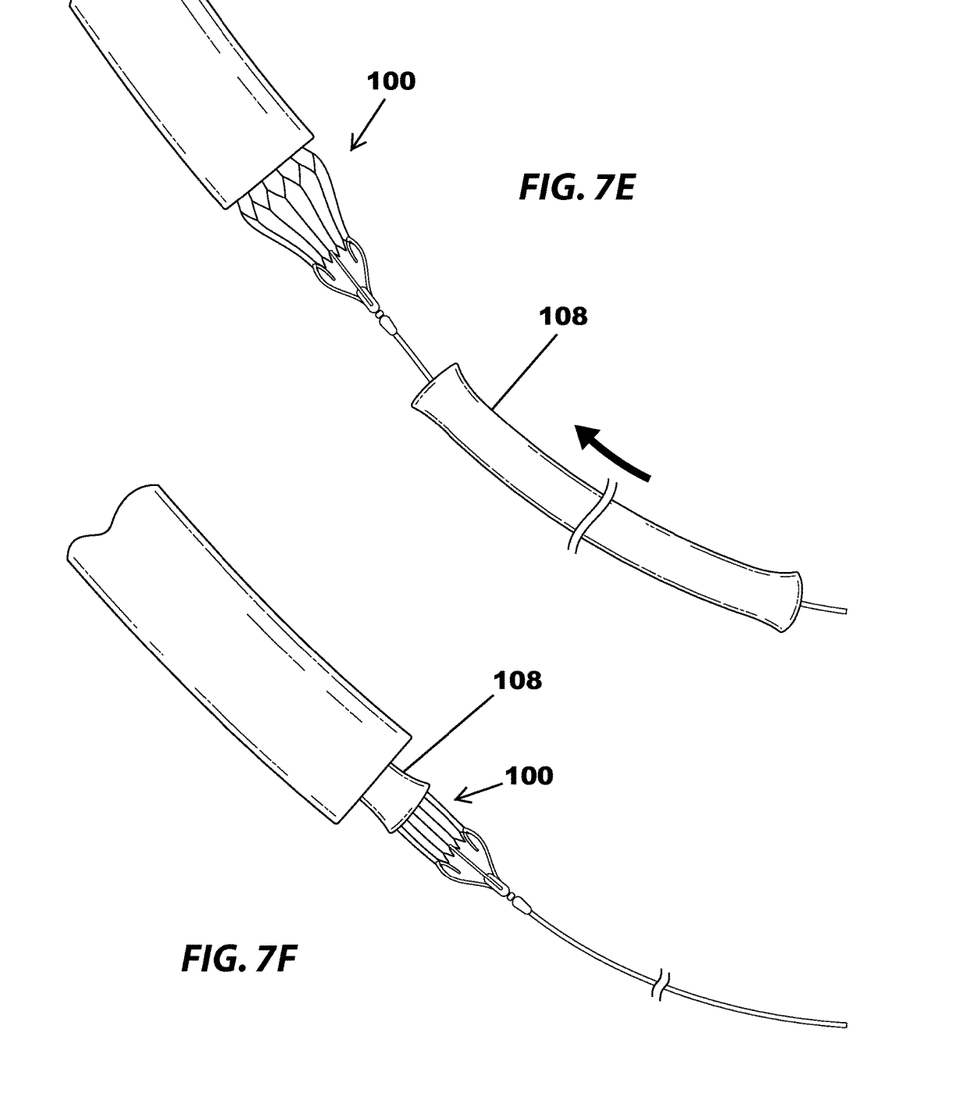

FIGS. 7A-7F illustrate an exemplary series of steps involved in removing the embolism protection device of FIGS. 1A and 1B from the body after a TAVR procedure has been performed, in accordance with various embodiments. These include identifying the flared proximal end 106 of the embolism protection device 100 (FIG. 7A) which extends outside the body, through the puncture site in the femoral artery, manually pinching the flared proximal end 106 of the embolism protection device 100 (FIG. 7B) to crimp the proximal end 106 (FIG. 7C), securing the crimped proximal end 106 of the embolism protection device 100 with a snare or hook member 114 (FIG. 7D), advancing the deployment/retrieval catheter 108 over the embolism protection device 100 (FIG. 7E), and removing the collapsed embolism protection device 100 and deployment/retrieval catheter 108 from the body of the subject (FIG. 7F).

In one specific, non-limiting example, an embolism protection device in accordance with the present disclosure may be used to protect the brain of a subject undergoing a TAVR procedure or other percutaneous valve procedure. In this example, a guidewire may be advanced through the vasculature using a right femoral artery approach, passing through the right iliac artery and terminating in the aorta, for instance just proximal to the aortic valve. A deployment catheter may be advanced along the guidewire until its distal end is positioned adjacent the aortic valve, and an embolism protection device may then be advanced in a collapsed state within the deployment catheter until the distal end of the embolism protection device is in aorta, adjacent the aortic valve. The deployment catheter may then be withdrawn, allowing the compliant wire support frame to self-expand and stretch the mesh sleeve of the embolism protection device into a hollow tube, covering the ostia of some or all of the major branches arising from the aorta.

A TAVR or other procedure may then be performed, and the inner surface of the mesh sleeve may capture potential emboli, while still allowing blood to flow freely through the mesh material. Once the procedure has been completed, a retrieval catheter may be advanced over the embolism protection device, causing it to collapse inside the lumen of the catheter. In this collapsed state, the embolism protection device and retrieval catheter may be withdrawn, along with or followed by the guidewire.

In another specific, non-limiting example, a guidewire may be advanced through the vasculature as described above, with the distal end of the guidewire coming to rest just proximal to the aortic valve. A deployment/retrieval catheter that contains a collapsed embolism protection device in its lumen may be advanced along the guidewire until the distal ends of both deployment/retrieval catheter and embolism protection device are positioned adjacent the aortic valve. The deployment/retrieval catheter may then be withdrawn, leaving the embolism protection device in place and allowing the compliant wire support frame to self-expand and stretch the mesh sleeve of the embolism protection device into a hollow tube, covering the ostia of some or all of the major branches arising from the aorta.

A TAVR or other procedure may then be performed, and the inner surface of the mesh sleeve may capture potential emboli, while still allowing blood to flow freely through the mesh material. Once the procedure has been completed, the deployment/retrieval catheter may be advanced once again over the embolism protection device, causing it to collapse inside the lumen of the catheter. In this collapsed state, the embolism protection device and deployment/retrieval catheter may be withdrawn, along with or followed by the guidewire.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. An intravascular embolism protection device comprising:
   a hollow tube comprising:
      an elongated, compliant wire frame comprising a material having a shape-memory function; and
      an elongated mesh sleeve having an outer surface and an inner lumen, the elongated, compliant, wire frame being disposed within the inner lumen, the mesh sleeve having a pore size selected to allow blood to pass therethrough while restricting the passage of potential emboli;
   wherein the embolism protection device has a collapsed state wherein the embolism protection device fits within the lumen of a catheter, and an expanded state wherein the embolism protection device forms the hollow tube that spans the width of an aorta and extends from an aortic valve to a puncture site in a femoral artery, and wherein the hollow tube has a length dimension of at least 700 mm.

2. The intravascular embolism protection device of claim 1, wherein the hollow tube has a length dimension of at least 750 mm.

3. The intravascular embolism protection device of claim 1, wherein the hollow tube has a width dimension of 10-40 mm.

4. The intravascular embolism protection device of claim 1, wherein the mesh material has a pore size of 80-100 microns.

5. The intravascular embolism protection device of claim 1, wherein the mesh material has a pore size of 100 microns.

6. The intravascular embolism protection device of claim 1, wherein the hollow tube covers the ostia of at least four arterial branches arising from the aorta.

7. The intravascular embolism protection device of claim 1, wherein the elongated, compliant, wire frame comprises a proximal end and a distal end, and wherein the distal end is flared radially outward.

8. A kit for preventing embolisms during a TAVR procedure, the kit comprising:

a first catheter having a proximal end and a distal end and being sized to span a distance between an aortic valve and a puncture site in a femoral artery;

an intravascular embolism protection device comprising:
a hollow tube comprising:
an elongated, compliant wire frame comprising a material having a shape-memory function; and
an elongated mesh sleeve having an outer surface and an inner lumen, the elongated, compliant, wire frame being disposed within the inner lumen, the mesh sleeve having a pore size selected to allow blood to pass therethrough while restricting the passage of potential emboli;
wherein the embolism protection device comprises a proximal end and a distal end, and has a collapsed state wherein the embolism protection device fits within the lumen of the first catheter, and an expanded state wherein the embolism protection device forms the hollow tube that spans the width of an aorta and extends from an the aortic valve to the puncture site in a femoral artery, and wherein the hollow tube has a length dimension of at least 700 mm.

9. The kit of claim 8, wherein the first catheter and the hollow tube both extend out of the puncture site in the femoral artery when a distal end of the embolism protection device is positioned adjacent the aortic valve.

10. The kit of claim 8, wherein the first catheter is a deployment catheter, and wherein the proximal end is flared radially outward.

11. The kit of claim 10, wherein the kit further comprises a second catheter having a proximal end and a distal end and being sized to span a distance between an aortic valve and a puncture site in a femoral artery, wherein the second catheter is a retrieval catheter.

12. The kit of claim 11, wherein the retrieval catheter has a distal end that is flared radially outward.

13. The kit of claim 8, wherein the first catheter is a deployment/retrieval catheter, and wherein one of the first and second ends is flared radially outward.

14. The kit of claim 8, wherein the first catheter is a deployment/retrieval catheter, and wherein both the proximal and distal ends are flared radially outward.

* * * * *